US011629186B2

(12) United States Patent
Kiaris et al.

(10) Patent No.: US 11,629,186 B2
(45) Date of Patent: *Apr. 18, 2023

(54) ANTI-CCL8 ANTIBODIES AND USES THEREOF

(71) Applicant: UNIVERSITY OF SOUTH CAROLINA, Columbia, SC (US)

(72) Inventors: Hippokratis Kiaris, Irmo, SC (US); Eleni Farmaki, Columbia, SC (US); Ioulia Chatzistamou, Irmo, SC (US); Vimala Kaza, Lexington, SC (US)

(73) Assignee: University of South Carolina, Columbia, SC (US)

( * ) Notice: Subject to any disclaimer, the term of this patent is extended or adjusted under 35 U.S.C. 154(b) by 387 days.

This patent is subject to a terminal disclaimer.

(21) Appl. No.: 16/895,407

(22) Filed: Jun. 8, 2020

(65) Prior Publication Data

US 2020/0299374 A1    Sep. 24, 2020

Related U.S. Application Data

(63) Continuation of application No. 16/371,386, filed on Apr. 1, 2019, now Pat. No. 10,723,794, which is a continuation-in-part of application No. 15/072,643, filed on Mar. 17, 2016, now abandoned.

(60) Provisional application No. 62/134,820, filed on Mar. 18, 2015.

(51) Int. Cl.

| A61K 39/395 | (2006.01) |
| C07K 16/24 | (2006.01) |
| C07K 16/30 | (2006.01) |
| A61K 45/06 | (2006.01) |
| C12Q 1/686 | (2018.01) |
| A61K 39/00 | (2006.01) |

(52) U.S. Cl.

CPC ........ *C07K 16/24* (2013.01); *A61K 39/39558* (2013.01); *A61K 45/06* (2013.01); *C07K 16/3015* (2013.01); *C12Q 1/686* (2013.01); *A61K 2039/545* (2013.01); *C07K 2317/76* (2013.01)

(58) Field of Classification Search

None
See application file for complete search history.

(56) References Cited

U.S. PATENT DOCUMENTS

| 4,522,811 A | 6/1985 | Eppstein et al. |
| 4,868,116 A | 9/1989 | Morgan et al. |
| 4,980,286 A | 12/1990 | Morgan et al. |
| 5,135,917 A | 8/1992 | Burch |
| 5,168,053 A | 12/1992 | Altman et al. |
| 5,176,996 A | 1/1993 | Hogan et al. |
| 5,334,711 A | 8/1994 | Sproat et al. |
| 5,476,766 A | 12/1995 | Gold et al. |
| 5,543,293 A | 8/1996 | Gold et al. |
| 5,580,967 A | 12/1996 | Joyce |
| 5,595,873 A | 1/1997 | Joyce |
| 5,624,824 A | 4/1997 | Yuan et al. |
| 5,631,115 A | 5/1997 | Ohtsuka et al. |
| 5,646,042 A | 7/1997 | Stinchcomb et al. |
| 5,652,107 A | 7/1997 | Lizardi et al. |
| 5,683,873 A | 11/1997 | George et al. |
| 5,683,874 A | 11/1997 | Kool |
| 5,728,521 A | 3/1998 | Yuan et al. |
| 5,861,254 A | 1/1999 | Schneider et al. |
| 5,861,288 A | 1/1999 | Usman et al. |
| 5,869,248 A | 2/1999 | Yuan et al. |
| 5,869,253 A | 2/1999 | Draper |
| 5,874,566 A | 2/1999 | Veerapanane et al. |
| 5,877,162 A | 3/1999 | Werner et al. |
| 5,910,408 A | 6/1999 | Szostak et al. |
| 5,962,426 A | 10/1999 | Glazer |
| 5,989,906 A | 11/1999 | Thompson |
| 5,994,320 A | 11/1999 | Low et al. |
| 6,017,756 A | 1/2000 | Draper |
| 6,022,962 A | 2/2000 | Chowrira et al. |
| 6,030,776 A | 2/2000 | Eaton et al. |
| 6,046,319 A | 4/2000 | Power et al. |
| 6,051,698 A | 4/2000 | Janjic et al. |
| 6,057,437 A | 5/2000 | Kamiya et al. |
| 6,562,347 B1 | 5/2003 | Kwak et al. |
| 9,528,998 B2 * | 12/2016 | Yoshimura ......... G01N 33/6803 |
| 2011/0082185 A1 | 4/2011 | Caballero et al. |
| 2011/0287036 A1 | 11/2011 | Matsumura et al. |
| 2012/0214864 A1 | 8/2012 | Richer et al. |

(Continued)

FOREIGN PATENT DOCUMENTS

| CN | 102319241 | 1/2012 |
| JP | 2010-229038 | 10/2010 |

(Continued)

OTHER PUBLICATIONS

Almagro, et al. "Humanization of antibodies" *Front. Biosci.* 13 (2008) pp. 1619-1633.
Bedford, et al. "Peromyscus mice as a model for studying natural variation" *eLife* 4:e06813 (2015) pp. 1-13.
Bennett, et al. "Evaluation of cyclosporine-treated mice as hosts for growing and testing the chemosensitivity of first-transplant-generation human tumor xenografts implanted under the kidney capsule" *J Natl Cancer Inst.* 75(5) (1985) pp. 925-936, (Abstract only).
Bhowmick, et al. "TGF-β signaling in fibroblasts modulates the oncogenic potential of adjacent epithelia" *Science* 303(5659) (2004) pp. 848-851.

(Continued)

*Primary Examiner* — Meera Natarajan
(74) *Attorney, Agent, or Firm* — Dority & Manning, P.A.

(57) ABSTRACT

Anti-CCL8 antibodies and antigen binding fragments thereof are described. Antibodies and fragments thereof can be used for prevention of migration of breast cancer cells. Methods include delivery of an anti-CCL8 antibody or an antigen binding fragment thereof to an area including the breast cancer cells, e.g., delivery to a subject in need thereof in an effective amount.

20 Claims, 10 Drawing Sheets

Specification includes a Sequence Listing.

(56) References Cited

U.S. PATENT DOCUMENTS

| | | | |
|---|---|---|---|
| 2013/0189367 A1 | 7/2013 | Zhang et al. |
| 2013/0251752 A1 | 9/2013 | Antonia et al. |
| 2013/0261058 A1 | 10/2013 | Schally et al. |
| 2014/0186468 A1 | 7/2014 | Gonzalo et al. |
| 2014/0303133 A1 | 10/2014 | Pientenpol et al. |
| 2016/0272702 A1 | 9/2016 | Kiaris et al. |

FOREIGN PATENT DOCUMENTS

| | | |
|---|---|---|
| WO | WO 89/07136 | 8/1989 |
| WO | WO 90/02806 | 3/1990 |
| WO | WO 97/18312 | 5/1997 |
| WO | WO 98/58058 | 12/1998 |
| WO | WO 2008/052566 | 5/2008 |

OTHER PUBLICATIONS

Churchill, et al. "The Collaborative Cross, a community resource for the genetic analysis of complex traits" *Nat. Genet.* 36 (2004) pp. 1133-1137.

Day, et al. "Preclinical mouse cancer models: a maze of opportunities and challenges." *Cell* 163(1) (2015) pp. 39-53.

De Genst, et al. "Antibody repertoire development in camelids" *Develop. Comp. Immun.* 30 (2006) pp. 187-198.

Farmaki, et al. "A Ccl8 gradient drives breast cancer cell dissemination" *Oncogene* 35(49) (2016) pp. 6309-6318.

Fidler, I.J. "The pathogenesis of cancer metastasis: the 'seed and soil' hypothesis revisited" *Nat Rev Cancer* 3 (2003) pp. 453-458.

Fingert, et al. "Transplantation of human or rodent tumors into cyclosporine-treated mice: a feasible model for studies of tumor biology and chemotherapy" *Proc Natl Acad Sci USA* 81(24) (1984) pp. 7927-7931.

Goodman, et al. "A model of human melanoma in cyclosporine-immunosuppressed rats" *J Invest Dermatol.* 88(2) (1987) pp. 141-144.

Havighorst, et al. "*Peromyscus* as a model of human disease" *Seminars in Cell and Developmental Biology* 61 (2017) pp. 150-155, (Abstract only).

Hori, et al. "CCL8 is a potential molecular candidate for the diagnosis of graft-versus-host disease" *Blood* 111(8) (2008) pp. 4403-4412.

Lebleu, et al. "PGC-1α mediates mitochondrial biogenesis and oxidative phosphorylation in cancer cells to promote metastasis" *Nat Cell Biol.* 16(10) (2014) pp. 992-1003.

Ota, et al. "Upregulation of plasma CCL8 in mouse model of graft-vs-host disease" *Exp Hematol.* 37(4) (2009) pp. 525-531.

Pitteri, et al. "Tumor Microenvironment-Derived Proteins Dominate the Plasma Proteome Response During Breast Cancer Induction and Progression" *Cancer Research* 71(15) (2011) pp. 5090-5100.

Rajaram, et al. "System-wide analysis reveals a complex network of tumor-fibroblast interactions involved in tumorigenicity" *PLoS Genet.* 9(9):e1003789 (2013) pp. 1-16.

Svenson, et al. "High-resolution genetic mapping using the mouse diversity outbred population" *G.A. Genetics* 190 (2012) pp. 437-447.

Taub, et al. "Monocyte chemotactic protein-1 (MCP-1), -2, and -3 are chemotactic for human T lymphocytes" *J. Clin. Invest.* 95 (1995) pp. 1370-1376.

Torres, et al. "Proteome profiling of cancer-associated fibroblasts identifies novel proinflammatory signatures and prognostic markers for colorectal cancer" *Clin Cancer Res.* 19(21) (2013) pp. 6006-6019.

Vanharanta, et al. "Origins of metastatic traits" *Cancer Cell* 24(4) (2013) pp. 410-421.

Wade, et al. "Genetic variation in laboratory mice" *Nat Genet.* 7(11) (2005) pp. 1175-1180.

Yoshinaga, et al. "g L-chain Shuffling for Affinity Maturation of Phage Library-derived Human Anti-human MCP-1 Antibody Blocking its Chemotactic Activity" *J. Biochem.* 143 (2008) pp. 593-601.

* cited by examiner

SEQ ID NO: 3 - Heavy chain–variable region–DNA (402 BP)

ATGGAATGTAACTGGATACTTCCTTTTATTCTGTCGGTAATTTCAGGGGTCTACTCAGAGGTTC
AGCTCCAGCAGTCTGGGACTGTGCTGGCAAGGCCTGGGGCTTCCGTGAAGATGTCCTGTAAGGC
TTCTGGCTACAGCTTTACCAGCTACTGGATGCACTGGGTCAAACAGAGGCCTGGACAGGGTCTG
GAATGGATTGGTGCTATTTATCCTGGAAATAGTGATAGTGGCTACAATAAGAAGTTCAAGGGCA
AGGCCAAACTGACTGCAGTCACTTCCGCCAGCACTGCCTACATGGAGCTCAGCAGCTTGACAAA
TGAGGACTCTGCGGTCTATTACTGTTCCCATACAGCCTGGTTTGTTTACTGGGGCCAAGGGACT
CTGGTCACTGTCTCTGCA

SEQ ID NO: 4 - Heavy chain-variable region–amino acid (134 AA)

MECNWILPFILSVISGVYSEVQLQQSGTVLARPGASVKMSCKASGYSFTSYWMHWVKQRPGQGL
EWIGAIYPGNSDSGYNKKFKGKAKLTAVTSASTAYMELSSLTNEDSAVYYCSHTAWFVYWGQGT
LVTVSA

SEQ ID NO: 11 - Light chain 1–variable region–DNA (396 BP)
ATGATGAGTCCTGCCCAGTTCCTGTTTCTGTTAGTGCTCTGGATTCGGGAAACCAACGGTGATG
TTGTGATGACCCAGACTCCACTCACTTTGTCGGTTACCATTGGACAACCAGCCTCCATCTCTTG
CAAGTCAAGTCAGAGCCTCTTAGATAGTGATGGAAGGACATATTTGAATTGGTTGTTACAGAGG
CCAGGCCAGTCTCCAAAGCGCCTAATCTATCTGGTGTCTAAACTGGACTCTGGAGTCCCTGACA
GGTTCACTGGCAGTGGATCAGGGACAGATTTCACACTGAAAATCAGCAGAGTGGAGGCTGAGGA
TTTGGGAGTTTATTATTGCTGGCAAGGTGCACATTTTCCTCAGACGTTCGGTGGAGGCACCAAG
CTGGAAATCAAA SEQ ID NO: 12 - Light chain 1–variable region–amino acid (132 AA)
MMSPAQFLFLLVLWIRETNGDVVMTQTPLTLSVTIGQPASISCKSSQSLLDSDGRTYLNWLLQR
PGQSPKRLIYLVSKLDSGVPDRFTGSGSGTDFTLKISRVEAEDLGVYYCWQGAHFPQTFGGGTK
LEIK SEQ ID NO: 19 - Light chain 2–variable region–DNA (381 BP)
ATGAGGTTCCAGGTTCAGGTTCTGGGGCTCCTTCTGCTCTGGATATCAGGTGCCCAGTGTGATG
TCCAGATAACCCAGTCTCCATCTTATCTTGCTGCATCTCCTGGAGAAACCATTACTTTTAATTG
CAGGGCAAGTAAGAGCATTAGCAAATATTTCGCCTGGTATCAAGAGAAACCTGGGAAAACTAAT
AAGCTTCTTATCTACTCTGGATCCACTTTGCAATCTGGAATTCCATCAAGGTTCAGTGGCAGTG
GATCTGGTACAGATTTCAATCTCACCATCAGTAGCCTGGAGCCTGAAGATTTTGCAATGTATTA
CTGTCAACAGCATAATGAATACCCGCTCACGTTCGGTGCTGGGACCAAGCTGGAGCTGAAA SEQ ID NO: 20 - Light chain 2–variable region–amino acid (127 AA)
MRFQVQVLGLLLLWISGAQCDVQITQSPSYLAASPGETITFNCRASKSISKYFAWYQEKPGKTN
KLLIYSGSTLQSGIPSRFSGSGSGTDFNLTISSLEPEDFAMYYCQQHNEYPLTFGAGTKLELK

FIG. 2

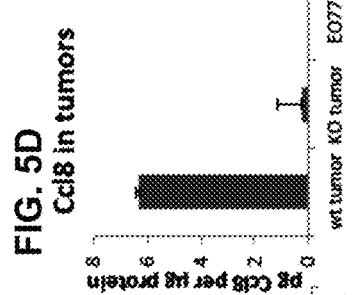
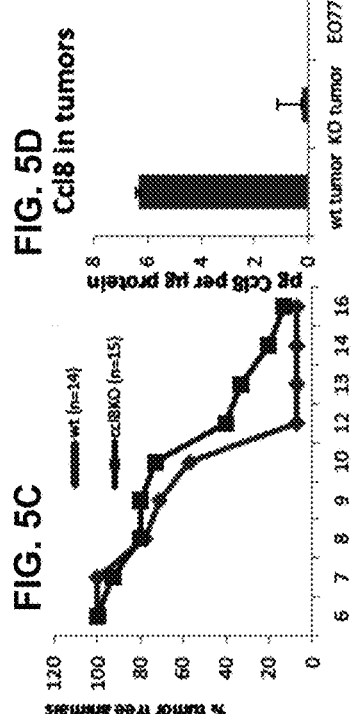
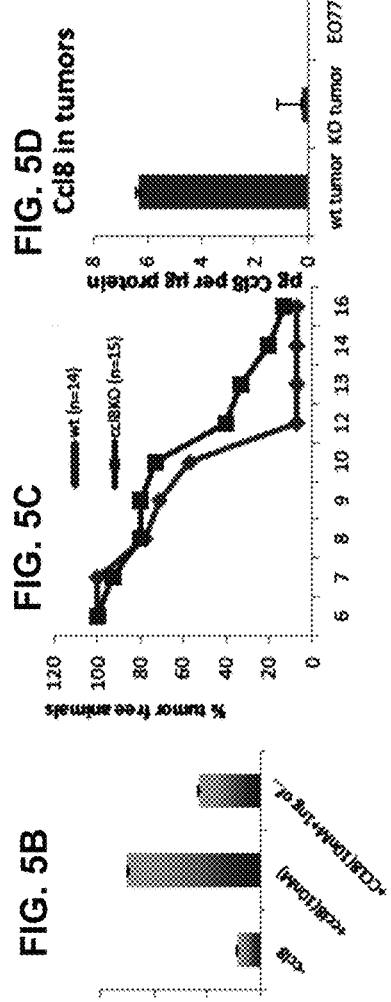
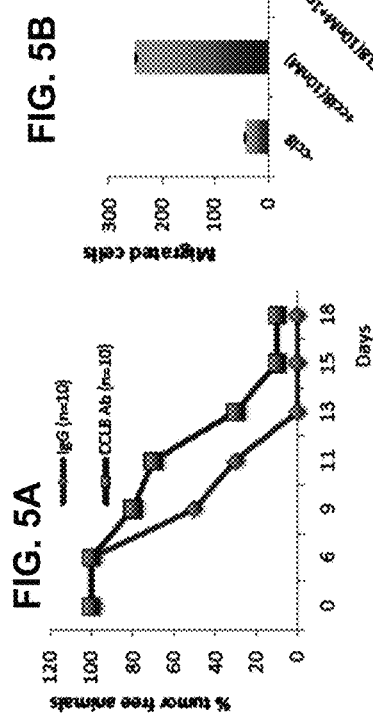
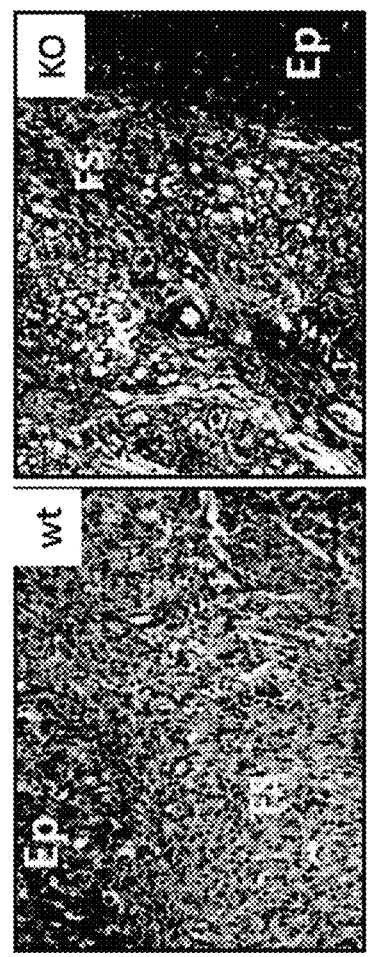
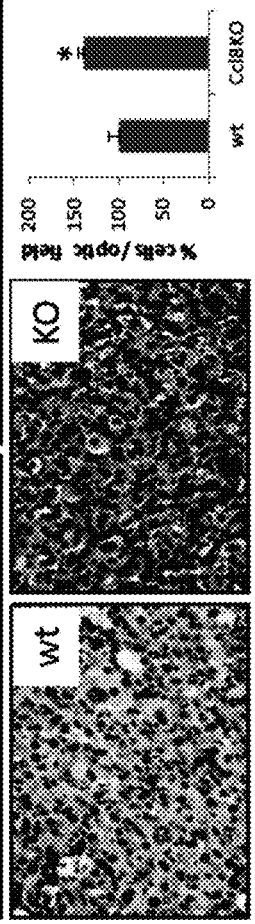
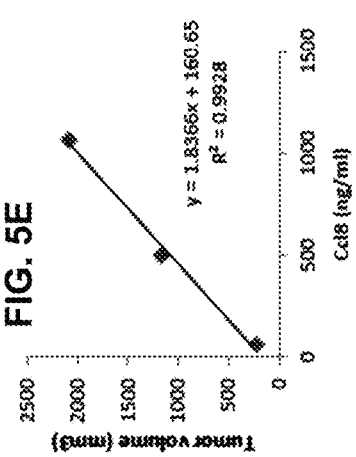
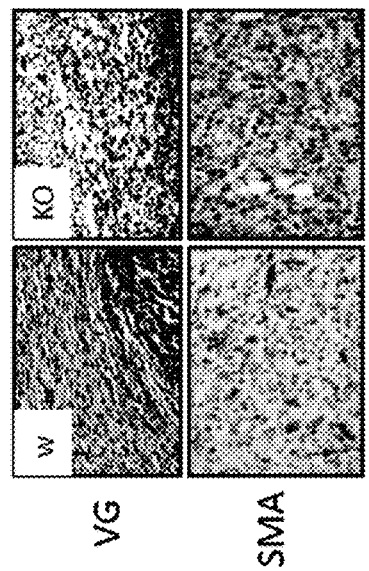

hCCL8: 1ng/ml
hCCL7: 10 ng/ml
hCCL11: 10 ng/ml

SEQUENCE LISTING

```
<160> NUMBER OF SEQ ID NOS: 26

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Ile Asn Arg Lys Ile Pro Ile Gln Arg Leu Glu Ser Tyr Thr
1               5                   10                  15
```

-continued

<210> SEQ ID NO 2
<211> LENGTH: 99
<212> TYPE: PRT
<213> ORGANISM: Homo sapiens

<400> SEQUENCE: 2

Met Lys Val Ser Ala Ala Leu Leu Cys Leu Leu Met Ala Ala Thr
1               5                   10                  15

Phe Ser Pro Gln Gly Leu Ala Gln Pro Asp Ser Val Ser Ile Pro Ile
            20                  25                  30

Thr Cys Cys Phe Asn Val Ile Asn Arg Lys Ile Pro Ile Gln Arg Leu
        35                  40                  45

Glu Ser Tyr Thr Arg Ile Thr Asn Ile Gln Cys Pro Lys Glu Ala Val
    50                  55                  60

Ile Phe Lys Thr Lys Arg Gly Lys Glu Val Cys Ala Asp Pro Lys Glu
65                  70                  75                  80

Arg Trp Val Arg Asp Ser Met Lys His Leu Asp Gln Ile Phe Gln Asn
                85                  90                  95

Leu Lys Pro

<210> SEQ ID NO 3
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggaatgta actggatact tccttttatt ctgtcggtaa tttcaggggt ctactcagag    60
gttcagctcc agcagtctgg gactgtgctg gcaaggcctg ggcttccgt gaagatgtcc    120 tgtaaggctt ctggctacag ctttaccagc tactggatgc actgggtcaa acagaggcct   180
ggacagggtc tggaatggat tggtgctatt tatcctggaa atagtgatag tggctacaat   240
aagaagttca agggcaaggc caaactgact gcagtcactt ccgccagcac tgcctacatg   300
gagctcagca gcttgacaaa tgaggactct gcggtctatt actgttccca tacagcctgg   360
tttgtttact ggggccaagg gactctggtc actgtctctg ca                      402

<210> SEQ ID NO 4
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Glu Cys Asn Trp Ile Leu Pro Phe Ile Leu Ser Val Ile Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Ser Phe
        35                  40                  45

Thr Ser Tyr Trp Met His Trp Val Lys Gln Arg Pro Gly Gln Gly Leu
    50                  55                  60

Glu Trp Ile Gly Ala Ile Tyr Pro Gly Asn Ser Asp Ser Gly Tyr Asn
65                  70                  75                  80

Lys Lys Phe Lys Gly Lys Ala Lys Leu Thr Ala Val Thr Ser Ala Ser

```
                    85                  90                  95
Thr Ala Tyr Met Glu Leu Ser Ser Leu Thr Asn Glu Asp Ser Ala Val
            100                 105                 110

Tyr Tyr Cys Ser His Thr Ala Trp Phe Val Tyr Trp Gly Gln Gly Thr
        115                 120                 125

Leu Val Thr Val Ser Ala
    130
```

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agctactgga tgcac                                                        15

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ser Tyr Trp Met His
1               5
```

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gctatttatc ctggaaatag tgatagtggc tacaataaga agttcaaggg c                51

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Ala Ile Tyr Pro Gly Asn Ser Asp Ser Gly Tyr Asn Lys Lys Phe Lys
1               5                   10                  15

Gly
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acagcctggt ttgtttac                                                     18

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ala Trp Phe Val Tyr
1               5

<210> SEQ ID NO 11
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgatgagtc ctgcccagtt cctgtttctg ttagtgctct ggattcggga aaccaacggt      60
gatgttgtga tgacccagac tccactcact ttgtcggtta ccattggaca accagcctcc     120
atctcttgca agtcaagtca gagcctctta gatagtgatg gaaggacata tttgaattgg     180
ttgttacaga ggccaggcca gtctccaaag cgcctaatct atctggtgtc taaactggac     240
tctggagtcc ctgacaggtt cactggcagt ggatcaggga cagatttcac actgaaaatc     300
agcagagtgg aggctgagga tttgggagtt tattattgct ggcaaggtgc acatttcct     360 cagacgttcg gtggaggcac caagctggaa atcaaa                              396

<210> SEQ ID NO 12
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Met Ser Pro Ala Gln Phe Leu Phe Leu Leu Val Leu Trp Ile Arg
1               5                  10                  15

Glu Thr Asn Gly Asp Val Val Met Thr Gln Thr Pro Leu Thr Leu Ser
                20                  25                  30

Val Thr Ile Gly Gln Pro Ala Ser Ile Ser Cys Lys Ser Ser Gln Ser
            35                  40                  45

Leu Leu Asp Ser Asp Gly Arg Thr Tyr Leu Asn Trp Leu Leu Gln Arg
        50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Ala His Phe Pro Gln Thr Phe Gly Gly Gly Thr Lys
        115                 120                 125

Leu Glu Ile Lys
    130

```
<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aagtcaagtc agagcctctt agatagtgat ggaaggacat atttgaat            48

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Ser Ser Gln Ser Leu Leu Asp Ser Asp Gly Arg Thr Tyr Leu Asn
1               5                   10                  15

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctggtgtcta aactggactc t                                          21

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Val Ser Lys Leu Asp Ser
1               5

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggcaaggtg cacattttcc tcagacg                                    27

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Gln Gly Ala His Phe Pro Gln Thr
1               5
```

<210> SEQ ID NO 19
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atgaggttcc aggttcaggt tctggggctc cttctgctct ggatatcagg tgcccagtgt    60
gatgtccaga taacccagtc tccatcttat cttgctgcat ctcctggaga aaccattact   120
tttaattgca gggcaagtaa gagcattagc aaatatttcg cctggtatca agagaaacct   180
gggaaaacta ataagcttct tatctactct ggatccactt tgcaatctgg aattccatca   240
aggttcagtg gcagtggatc tggtacagat ttcaatctca ccatcagtag cctggagcct   300
gaagattttg caatgtatta ctgtcaacag cataatgaat acccgctcac gttcggtgct   360
gggaccaagc tggagctgaa a                                             381
```

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Arg Phe Gln Val Gln Val Leu Gly Leu Leu Leu Leu Trp Ile Ser
1               5                   10                  15
Gly Ala Gln Cys Asp Val Gln Ile Thr Gln Ser Pro Ser Tyr Leu Ala
            20                  25                  30
Ala Ser Pro Gly Glu Thr Ile Thr Phe Asn Cys Arg Ala Ser Lys Ser
        35                  40                  45
Ile Ser Lys Tyr Phe Ala Trp Tyr Gln Glu Lys Pro Gly Lys Thr Asn
    50                  55                  60
Lys Leu Leu Ile Tyr Ser Gly Ser Thr Leu Gln Ser Gly Ile Pro Ser
65                  70                  75                  80
Arg Phe Ser Gly Ser Gly Ser Gly Thr Asp Phe Asn Leu Thr Ile Ser
                85                  90                  95
Ser Leu Glu Pro Glu Asp Phe Ala Met Tyr Tyr Cys Gln Gln His Asn
            100                 105                 110
Glu Tyr Pro Leu Thr Phe Gly Ala Gly Thr Lys Leu Glu Leu Lys
        115                 120                 125
```

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
agggcaagta agagcattag caaatatttc gcc                                 33
```

<210> SEQ ID NO 22
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 22

Arg Ala Ser Lys Ser Ile Ser Lys Tyr Phe Ala
1               5                   10

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tctggatcca ctttgcaatc t                                               21

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Gly Ser Thr Leu Gln Ser
1               5

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
caacagcata atgaataccc gctcacg                                         27

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln His Asn Glu Tyr Pro Leu Thr
1               5
```

ANTI-CCL8 ANTIBODIES AND USES THEREOF

CROSS REFERENCE TO RELATED APPLICATION

This application is a continuation application of U.S. patent application Ser. No. 16/371,386, having a filing date of Apr. 1, 2019, entitled "Anti-CCL8 Antibodies and Uses Thereof;" which is a continuation-in-part application of U.S. patent application Ser. No. 15/072,643 having a filing date of Mar. 17, 2016 entitled "Anti-CCL8 Therapy for Breast Cancer;" which claims filing benefit of U.S. Provisional Patent Application Ser. No. 62/134,820 entitled "Anti-Ccl8 Therapy for Metastatic Breast Cancer," having a filing date of Mar. 18, 2015; all of which are incorporated herein by reference for all purposes.

GOVERNMENT SUPPORT CLAUSE

This invention was made with government support under 5P30GM103336-02 awarded by the National Institutes of Health. The government has certain rights in the invention.

SEQUENCE LISTING

This application contains a Sequence Listing which is being filed electronically in ASCII format concurrently herewith and is hereby incorporated by reference in its entirety. Said ASCII copy, created on Jul. 25, 2019, is named USC-470-CIPCON_Sequence List.txt and is 11,618 bytes in size.

BACKGROUND

Tumor cell dissemination reflects the collective outcome of multiple events that include the invasion of the cancer cells into the surrounding stroma, subsequently their intravasation and entrance into circulation, and ultimately their extravasation and seeding into the sites of secondary growth. It is conceivable that interference with the pathways that promote the dissemination of the cancer cells will inhibit metastases providing tools for disease management. Directed cell migration towards specific gradients of chemoattractive factors may provide a model to explain the spread of cancer cells and the initiation of the metastatic process. While this mechanism appears attractive in explaining cancer cell dissemination, details remain elusive, and useful treatment protocols based upon the mechanism likewise remain elusive.

Chemokines are a superfamily of small, cytokine-like proteins that are resistant to hydrolysis, promote neovascularization or endothelial cell growth inhibition, induce cytoskeletal rearrangement, activate or inactivate lymphocytes, and mediate chemotaxis through interactions with G-protein coupled receptors. Chemokines can mediate the growth and migration of host cells that express their receptors.

CCL8 is a small cytokine belonging to the CC chemokine family that attracts monocytes, lymphocytes, basophils and eosinophils. The processed form (generally referred to as MCP-2) is understood to activate many different immune cells, including mast cells, eosinophils and basophils implicated in allergic responses, and monocytes, T cells, and NK cells that are involved in the inflammatory response, and inhibits the chemotactic effect most predominantly of CCL7, but also of CCL2 and CCL5. CCL8 elicits its effects by binding to several different chemokine cell surface receptors including CCR1, CCR2B and CCR5. CCL8 can bind heparin and is believed to play a role in neoplasia and inflammatory host responses.

What are needed in the art are methods and materials for prevention of tumor cell dissemination. Methods and materials for use in aggressive cancers, such as triple-negative breast cancers would be of great benefit.

SUMMARY

Disclosed are anti-CCL8 antibodies and antigen-binding fragment thereof that specifically recognize and bind an epitope of CCL8. For instance, an anti-CCL8 antibody or antigen binding fragment thereof can include one or more CDR fragments selected from SEQ ID NOs: 6, 8, 10, 14, 16, 18, 22, 24, 26. Also disclosed are compositions that include an anti-CCL8 antibody or antigen-binding portion thereof in conjunction with a carrier, e.g., a pharmaceutical carrier.

Also disclosed are methods for utilizing the materials including a method for preventing the migration of breast cancer cells. More specifically, the method includes locating an anti-CCL8 antibody or antigen-binding fragment thereof in an area including breast cancer cells. For instance, the breast cancer cells can include estrogen-independent cells and, in one embodiment, triple negative breast cancer cells.

Also disclosed is a method for treatment of breast cancer that includes determining the level of CCL8 in the subject prior to the treatment process, which can provide information with regard to epithelial-mesenchymal transition and initiation of metastasis in the subject and then providing an anti-CCL8 antibody or fragment thereof to the subject.

BRIEF DESCRIPTION OF THE DRAWINGS

The present invention may be better understood with reference to the accompanying figures, in which:

FIG. 2 presents a heavy chain variable region nucleotide sequence (SEQ ID NO: 3) and amino acid sequence (SEQ ID NO: 4), a first light chain variable region nucleotide sequence (SEQ ID NO: 11) and amino acid sequence (SEQ ID NO: 12), and a second light chain variable region nucleotide sequence (SEQ ID NO: 19) and amino acid sequence (SEQ ID NO: 20) of anti-CCL8 antibodies described herein.

FIG. 5A illustrates a drop in EO771 tumor onset in wild type (wt) mice following administration of a neutralizing antibody for CCL8.

FIG. 5B illustrates the effect on migrated cells upon inhibition of CCL8 by a neutralizing antibody for CCL8 in RAW macrophages.

FIG. 5OC illustrates delay of EO771 tumor onset in mice following genetic ablation of CCL8.

FIG. 5D presents CCL8 levels in EO771 tumors developed in wt and CCL8KO mice and in EO771 cells cultured in vitro.

FIG. 5E illustrates correlation between serum CCL8 levels and tumor volume in EO771 breast cancer-bearing mice.

FIG. 5F compares EO771 tumors in CCL8KO and wt mice.

FIG. 5G illustrates SMA immunostaining and Van Gieson staining of EO771 tumors in control and CCL8 knockout (CCL8KO) mice.

DETAILED DESCRIPTION

Figure 1:
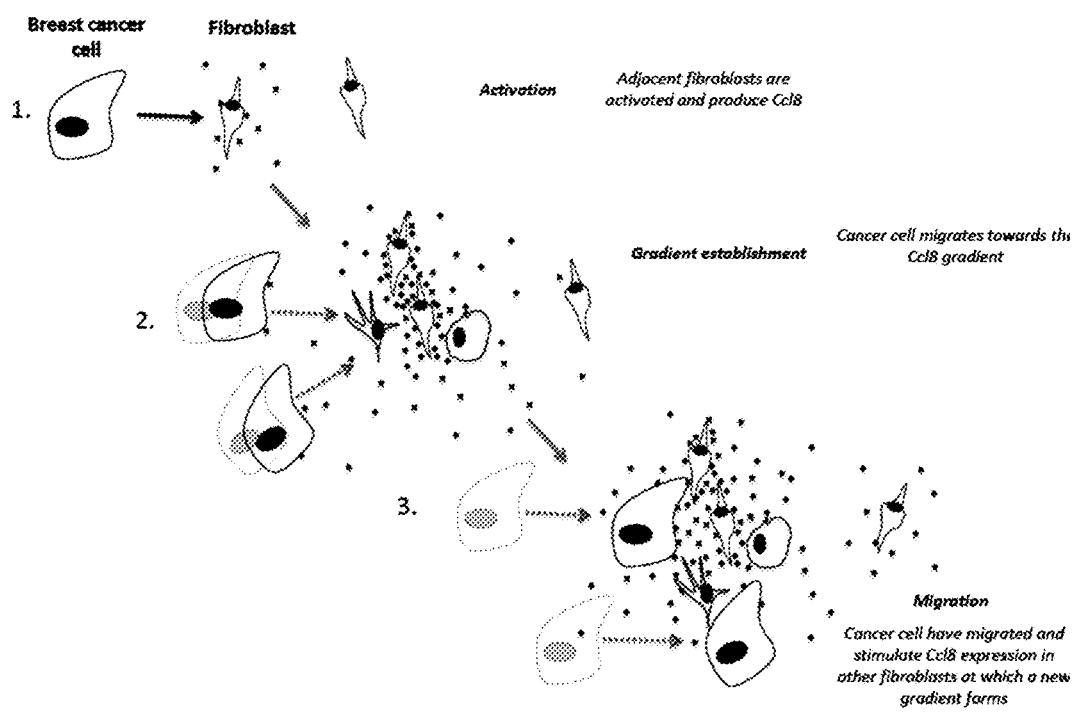
FIG. 1 presents a diagrammatic illustration of a breast cancer dissemination process in which a gradient of CCL8 is self-sustained to promote dissemination of the breast cancer cells.

The following description and other modifications and variations to the presently disclosed subject matter may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the following description is by way of example only and is not intended to limit the disclosed subject matter.

In general, disclosed herein are anti-CCL8 antibodies and methods and materials for prevention of migration of breast cancer cells. Disclosed methods and materials have been developed through recognition that a gradient of increasing CCL8 concentration is maintained from the epithelium towards the stroma and this gradient can be encouraged by breast cancer cells and instrumental for cancer cell dissemination. In one particular embodiment, the disclosed methods can be utilized in treatment of breast cancer.

The terms "treat," "treating," or "treatment" as used herein, refers to a method of alleviating or abrogating a disorder and/or its attendant symptoms. The terms "prevent," "preventing," or "prevention," as used herein, refer to a method of barring a subject from acquiring a disorder and/or its attendant symptoms. In certain embodiments, the terms "prevent," "preventing," or "prevention" refer to a method of reducing the risk of acquiring a disorder and/or its attendant symptom, e.g., metastatic breast cancer.

While not wishing to be bound to any particular theory, it is believed that CCL8 production by stromal fibroblasts can be upregulated in response to signals elicited by breast cancer cells, especially those from triple-negative breast cancers. Moreover, CCL8 can operate as a potent chemoattractant for various stromal and breast cancer cells, suggesting a role for CCL8 in the promotion of metastases. The presently disclosed methods and materials are directed to inhibition of CCL8 activity, which can inhibit the onset of cell dissemination from a tumor and can cause the development of well-confined lesions of increased cellularity and diminished stroma. The presently disclosed findings are consistent with the concept of an establishment of a self-sustained CCL8 gradient between cancer cells and fibroblasts that ultimately can promote breast cancer metastasis if left unchecked. Disruption of this gradient as disclosed herein can provide means for the management of breast cancers, and in one particular embodiment, estrogen-independent breast cancers such as triple-negative breast cancers.

It is hypothesized that soluble factors produced by the stroma in response to signals elicited by the epithelium may facilitate the establishment and maintenance of gradients that can stimulate the directional migration of cancer cells promoting tumor cell dissemination. Considering that the stromal cells produce these chemoattractive factors makes these gradients self-sustained, since the soluble factors' concentration will be higher distally than proximally to the cancer cells.

As described further herein, the chemokine CCL8 has emerged as a good candidate for participating in the establishment of such gradients because cancer cells have been found to stimulate CCL8 production in adjacent stromal fibroblasts. Furthermore, CCL8 has been identified by proteomic analyses as a stroma-derived protein in human cancers and its levels have been determined to be significantly elevated in the plasma of breast cancer-prone mice during disease progression. Finally, preliminary results have identified CCL8 as a target of Notch signaling, a pathway with strong paracrine activity.

A model for the role of CCL8 in cancer cell dissemination is illustrated in FIG. 1. As shown, it appears that soluble factors that are produced by the breast cancer cells can act on adjacent stromal fibroblasts to activate CCL8. Subsequently, CCL8 attracts the breast cancer cells that can now activate CCL8 in other fibroblasts generating a self-sustained gradient that ultimately promotes the dissemination of the cancer cells and metastasis. Accordingly, disclosed methods are generally directed to blockade of CCL8 activity so as to prevent cancer cell dissemination. Blockade of CCL8 activity can provide a strategy for breast cancer management and especially for the inhibition of metastases.

According to the present disclosure, breast cancer cell migration can be prevented by decreasing the activity of CCL8 in an area encompassing the breast cancer cells. CCL8 activity can be decreased by delivery of an anti-CCL8 antibody or antigen-binding fragment thereof to an area encompassing the breast cancer cells of interest. In one embodiment, a method can include administering to a subject diagnosed with breast cancer a therapeutically effective amount of the anti-CCL8 antibody or antigen-binding fragment thereof. For instance, the subject can be diagnosed with breast cancer and can exhibit elevated CCL8 expression in the stroma surrounding or in an area near a tumor.

In another embodiment, a method can include determining the level of CCL8 in a tissue from a subject and, if an increased level of CCL8 is detected administering to the subject an anti-CCL8 antibody or antigen-binding fragment thereof. According to one embodiment, determination of the level of CCL8 in a subject can be utilized as a biomarker for epithelial mesenchymal transition.

As used herein, the term "antibody" refers to immunoglobulin molecules and immunologically active portions of immunoglobulin (Ig) molecules, i.e., molecules that contain an antigen binding site that specifically binds (immunoreacts with) an antigen. The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. By "specifically bind" or "immunoreacts with" is meant that the antibody reacts with one or more antigenic determinants of the desired antigen and does not react (i.e., bind) with other polypeptides or binds at much lower affinity with other polypeptides. For instance, binding of the molecule to an epitope can be 2-fold greater or more, for instance from about 2-fold to about 5-fold greater, than the binding of the molecule to an unrelated epitope or than the binding of an unrelated molecule to the epitope, as determined by techniques known in the art, such as for example, ELISA, immunoprecipitation, two-hybrid assays, cold displacement assay, etc. Typically, specific binding can be distinguished from non-specific binding when the dissociation constant ($K_D$) is about $1 \times 10^{-5}$ M or less, or about $1 \times 10^{-6}$ M or less; for instance, about $1 \times 10^{-7}$ M in some embodiments.

The term "antibody" also includes antibody fragments that comprise a portion of a full-length antibody, generally the antigen binding or variable region thereof. Examples of antibody fragments include Fab, Fab', F(ab')2, and Fv fragments; diabodies; linear antibodies; single-chain antibody (scFv) molecules; and multispecific antibodies formed from antibody fragments. In certain embodiments of the invention, it may be desirable to use an antibody fragment, rather than an intact antibody, to increase tumor penetration, for example. In this case, it may be desirable to use an antibody fragment that has been modified by any means known in the art in order to increase its serum half-life.

The term "monoclonal antibody" as used herein refers to an antibody obtained from a population of substantially homogeneous antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An anti-CCL8 antibody is one that binds to human CCL8 and, preferably, blocks (partially or completely) the ability of breast cancer cells to bind or otherwise recognize CCL8. In one embodiment, the anti-CCL8 antibody is a monoclonal antibody. In another embodiment, the anti-CCL8 antibody is a humanized antibody. In another embodiment, the anti-CCL8 antibody is a humanized antibody fragment. "Humanized" forms of non-human antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody), such as mouse, rat, rabbit or nonhuman primate, having the desired specificity, affinity, and/or capacity. Methods for making humanized and other chimeric antibodies are known in the art.

A complete antibody can generally be comprised of two immunoglobulin heavy chains and two immunoglobulin light chains, each of which includes a variable region and a constant region. In one particular embodiment, an antibody as disclosed herein can include as heavy chain variable region ($V_H$) SEQ ID NO: 4, and as light chain variable region, either ($V_L$) SEQ ID NO: 12 or SEQ ID NO: 20. FIG. 2 presents the DNA sequences (SEQ ID NOs: 3, 11, and 19) of a heavy chain variable region, a first light chain variable region and a second light chain variable region, respectively, as well as the amino acid sequences (SEQ ID NOs: 4, 12, and 20) for the heavy chain variable region, the first light chain variable region and the second light chain variable region, respectively, of antibodies as disclosed herein. In FIG. 2, the leader sequence of each region is shown in bold font and the CDRs are underlined.

A complete antibody can include both a heavy chain and a light chain variable portion of the disclosed antibodies (SEQ ID NO: 4 ($V_H$) heavy chain and SEQ ID NO: 12 ($V_{L1}$) light chain, or SEQ ID NO: 4 ($V_H$) heavy chain and SEQ ID NO: 20 ($V_{L2}$) light chain) in conjunction with any suitable constant regions. In some embodiments, disclosed methods can utilize one or more isolated antigen binding portions of a complete antibody (e.g., one or more CDR regions SEQ ID NOs: 6, 8, 10, 14, 16, 18, 22, 24, 26), optionally in conjunction with their respective FR regions SEQ ID (underlined regions of SEQ ID NOs: 4, 12, 20 shown in FIG. 2). A CDR fragment can be provided in one embodiment bounded by one or both FR fragments as found in a complete variable region or alternatively can be utilized in an isolated format, independent of the natural FR fragments.

Antigen binding peptides as described herein can incorporate modifications as would be understood by one of skill in the art. For instance, there are many natural amino acids, which occur as L-isomers in most living organisms; however, embodiments of the disclosure are not limited to only L-amino acids and can include modifications that substitute D-amino acids or other non-proteinogenic amino acids that are not naturally encoded by humans or any other organism. Herein, unless specifically referenced as a D-amino acid (i.e. the amino acid identifier followed by (d)), reference to a generic amino acid indicates the L-amino acid.

In embodiments of the disclosure, an agent can include an ornithine substitution to disclosed peptides, e.g., to disclosed CDR fragments. In some embodiments, an agent can include one or more amino acid substitutions of a human proteinogenic amino acids selected from the following group: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In one embodiment, an agent can include structurally and/or functionally similar peptides to those disclosed herein. Structurally similar peptides can encompass variations such as the substitution of one amino acid having a first amino acid side chain with a second amino acid having a second amino acid side chain. Both the first amino acid side chain and the second amino acid side chain provide a similar characteristic to maintain functional similarity of the agent, i.e., CCL8 epitope binding. A similar characteristic can include a side chain that has a similar polarity, charge, or size as the first amino acid side chain. As an example, leucine includes a hydrophobic side chain, and in some embodiments, an agent can include substitution of a leucine of a disclosed sequence (e.g., a CDR sequence) with an isoleucine, valine, or alanine, as each of these amino acids includes a similar hydrophobic side chain. As another example, histidine includes an aromatic side chain that can also carry a positive charge, and in some embodiments, one or more histidines of a CCL8 binding antibody, or fragment thereof, can be substituted with an amino acid that includes an aromatic side chain or with an amino acid that can carry a positive charge such as phenylalanine, tyrosine, tryptophan, arginine, or lysine. These are provided as examples of possible substitutions and are not meant to limit the scope of variations contemplated by substituting amino acids that have similar side chain properties.

In some embodiments, the antigen binding fragments comprise a Fab, in which the fragment contains a monovalent antigen binding fragment of the antibody molecule, and which can be produced by digestion of whole antibody with the enzyme papain to yield an intact light chain variable region (e.g., SEQ ID NO: 12, SEQ ID NO: 20) and a portion of a heavy chain (e.g., one or more of SEQ ID NOs: 6, 8, 10), optionally in conjunction with one or more of the intervening FR fragments.

In one embodiment, the antigen binding fragment can comprise a Fab', which is the fragment of the antibody molecule that can be obtained by treating whole antibody with pepsin, followed by reduction, to yield an intact light chain or the variable region thereof (e.g., SEQ ID NO: 12, SEQ ID NO: 20) and a portion of the heavy chain (e.g., one or more of SEQ ID NOs: 6, 8, 10, optionally in conjunction with one or more of the intervening FR fragments); two Fab' fragments can be obtained per antibody molecule. A (Fab')2 fragment of the antibody is encompassed, which can be obtained by treating a whole antibody with the enzyme pepsin without subsequent reduction. A F(ab')2 fragment is a dimer of two Fab' fragments held together by two disulfide bonds. Also encompassed is a Fv, which is a genetically engineered fragment containing the variable region of the light chain and the variable region of the heavy chain expressed as two chains. In one embodiment, the antibody can encompass a single chain antibody ("SCA"), which is a genetically engineered molecule containing the variable region of the light chain and the variable region of the heavy chain, linked by a suitable polypeptide linker as a genetically fused single chain molecule. An antibody fragment can be an scFv-Fc, which is produced in one embodiment by fusing single-chain Fv (scFv) with a hinge region from an immunoglobulin (Ig) such as an IgG, and Fc regions.

An antibody or antigen binding fragment thereof can include a modification as is known in the art that does not interfere with the specific recognition and binding with the targeted epitope. For instance, a modification can minimize conformational changes during the shift from displayed to secreted forms of the antibody or fragment. As is understood by a skilled artisan, the modification can be a modification known in the art to impart a functional property that would not otherwise be present if it were not for the presence of the modification. The invention encompasses materials that are differentially modified during or after translation, e.g., by glycosylation, acetylation, phosphorylation, amidation, derivatization by known protecting/blocking groups, proteolytic cleavage, linkage to a particle, another molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH$_4$, acetylation, formylation, oxidation, reduction, metabolic synthesis in the presence of tunicamycin, etc.

A modification can include an N-terminus modification and/or a C-terminal modification. For example, the modification can include an N-terminus biotinylation and/or a C-terminus biotinylation. In one embodiment, the secretable form of the antibody or antigen binding fragment comprises an N-terminal modification that allows binding to an Immunoglobulin (Ig) hinge region. In another embodiment, the Ig hinge region is from but is not limited to, an IgA hinge region. In another embodiment, the secretable form of the antibody or antigen binding fragment comprises an N-terminal modification and/or a C-terminal modification that allows binding to an enzymatically biotinylatable site. In another embodiment biotinylation of said site can functionalize the site to bind to any surface coated with streptavidin, avidin, avidin-derived moieties, or a secondary reagent.

A modification can include, for example, addition of N-linked or O-linked carbohydrate chains, attachment of chemical moieties to the amino acid backbone, chemical modifications of N-linked or O-linked carbohydrate chains, and addition or deletion of an N-terminal methionine residue.

The antibodies or antigen binding fragments can be produced by any synthetic or recombinant process such as is well known in the art. The antibodies or antigen binding fragments can further be modified to alter biophysical or biological properties by means of techniques known in the art. For example, an antibody can be modified to increase its stability against proteases, or to modify its lipophilicity, solubility, or binding affinity to an epitope of, e.g., SEQ ID NO: 1 or SEQ ID NO: 2.

By way of example, the antibodies can be produced by the immunization of various animals, including mice, rats, rabbits, goats, primates, chickens and humans with a target antigen, such as an entire CCL8 sequence as described (SEQ ID NO: 2) or a peptide fragment of CCL8 containing one or more of sequences that include at least one anti-CCL8 epitope (e.g., SEQ ID NO: 1). In one embodiment, the antigen or peptide fragment containing the antigen can be purified prior to immunization of the animal. The antibody or antigen binding fragment obtained following the immunization can be purified by methods known in the art, for example, gel filtration, ion exchange, affinity chromatography, etc. Affinity chromatography or any of a number of other techniques known in the art can be used to isolate polyclonal or monoclonal antibodies from serum, ascites fluid, or hybridoma supernatants.

"Purified" means that the antibody is separated from at least some of the proteins normally associated with the antibody and preferably separated from all cellular materials other than proteins.

The antibodies or antigen binding fragments thereof may be produced by using gene recombination techniques. For example, in formation of a chimeric antibody, a humanized antibody, a functional fragment of antibody or the like such as an Fv, an SCA, an scFv-Fc or the like, genetic recombination techniques.

In one embodiment, a method for producing an agent that incorporates all or a portion of a variable region of a heavy chain (SEQ ID NO: 4) and a variable region of a light chain (SEQ ID NO: 12, SEQ ID NO: 20), e.g., including one or more CDR regions (SEQ ID NOs: 6, 8, 10, 14, 26, 18, 22, 24, 26), for instance in formation of a chimeric antibody, can be carried out through utilization of genetic recombination techniques.

By way of example, DNA encoding an amino acid sequence ($V_H$ region) represented by SEQ ID NO: 4 is prepared. Likewise, DNA encoding an amino acid sequence ($V_L$) represented by SEQ ID NO: 12 or SEQ ID NO: 20 is prepared. Examples of such DNA include those represented by SEQ ID NO: 3, SEQ ID NO: 11, and SEQ ID NO: 19, respectively; however, those having other nucleotide sequences may be used.

Portions or mutants of disclosed sequences, which still retain desired activity, are also considered within the scope of this disclosure. For example, mutants can include alterations to SEQ ID NOs: 3, 11, and 19 that encode one or more amino acid substitutions (e.g., mutating a codon for valine to a codon for alanine). Additionally, or alternatively, mutants of a DNA sequence can include one or more point mutations to the native cDNA sequence to substitute a degenerate codon for the native codon.

For embodiments that include a mutant of a nucleic acid sequence as disclosed (e.g., SEQ ID NOs: 3, 11, and 19 or portions thereof encoding a CDR region of an antibody including SEQ ID NOs: 5, 7, 9, 13, 15, 17, 21, 23, 25), the mutant can include one or more codon mutations that modify the expressed protein to substitute one hydrophobic amino acid (e.g., valine) for another hydrophobic amino acid (e.g., alanine, leucine, isoleucine, proline, phenylalanine, methionine, or tryptophan) to produce an antibody variant.

Due to codon redundancy, there are many theoretically possible cDNA sequence variants that could encode an antibody or antigen binding fragment as described herein. Additionally, variants that modify the native protein sequence, while retaining binding activity, further increase this number. For these embodiments, a genetic modification can result in the expression of a peptide (e.g., SEQ ID NO: 4) or a peptide variant that retains the binding function of the native peptide.

A DNA encoding $V_H$ (e.g., SEQ ID NO: 3) or $V_L$ (e.g., SEQ ID NO: 11, SEQ ID NO: 19) can be inserted into a vector having a sequence encoding the respective constant regions of a human antibody to construct a chimeric antibody expression vector. Vectors having a sequence encoding $C_H$ or $C_L$ of a human antibody as may be utilized are commercially available. By introducing the constructed expression vector into a host cell, a recombinant cell that expresses a chimeric antibody can be obtained. Following, the recombinant cell can be cultured, and a desired chimeric antibody can be acquired from the culture.

A host cell is not particularly limited as long as the expression vector is able to function therein. By way of example, animal cells (e.g., COS cells, CHO cells, HEK cells, and the like), yeast, bacteria (*Escherichia coli* and the like), plant cells, insect cells and the like may be appropriately employed.

In one embodiment, a recombination technique can be utilized to produce an antibody, including specific CDR including one or more of SEQ ID NOs: 6, 8, 10, 14, 16, 18, 22, 24, 26. For instance, a method can be utilized in forming a humanized antibody, which, as utilized herein refers to an antibody having a CDR derived from an animal other than human, and other regions (framework region, constant region and the like) derived from human.

For example, nucleotide sequences encoding heavy chain CDRs (SEQ ID NOs: 6, 8, 10) and light chain CDRs (SEQ ID NOs: 14, 16, 18, 22, 24, 26) of an antibody can be prepared. As the DNA, a sequence corresponding to each CDR nucleotide sequence represented by SEQ ID NOs: 5, 7, 9, 13, 15, 17, 21, 23, 25 is exemplified; however, as discussed above, those having other nucleotide sequences may be used. DNA may be prepared by known methods such as PCR. The DNA may be prepared by chemical synthesis.

Using these sequences, a sequence encoding a variable region in which heavy chain CDR encoding regions (e.g., SEQ ID NOs: 5, 7, 9) are grafted to the respective regions encoding framework regions (FR) of $V_H$ in a human antibody can be prepared. Likewise, sequences encoding a variable region in which light chain CDR encoding regions (e.g., SEQ ID NOs: 13, 15, 17, 21, 23, 25) are grafted to the respective regions encoding FR of $V_L$ in a human antibody can be prepared. The prepared nucleic acid sequence can then be inserted into a vector having a sequence encoding the desired constant region ($C_H$ or $C_L$) of a human antibody, so as to construct a humanized antibody expression vector. By introducing the constructed expression vector into a host cell, a recombinant cell that expresses a humanized antibody can obtained. The recombinant cell can then be cultured, and a desired humanized antibody can be acquired from the culture.

An agent including fewer than all of the CDRs of a full antibody can be produced in a similar procedure. For instance, an agent that includes only the $V_H$ or only the $V_L$ region of an antibody, absent the constant region can be produced in a similar fashion.

Methods for purifying an agent formed according methods as described herein are not particularly limited, and known techniques may be employed. For example, a culture supernatant of a hybridoma or a recombinant cell may be collected, and the antibody or antigen binding fragment may be purified by a combination of known techniques such as various kinds of chromatography, salt precipitation, dialysis, membrane separation and the like. When the isotype of the antibody is IgG, the antibody may be conveniently purified by affinity chromatography using protein A.

An agent may be administered to a subject according to known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In certain embodiments, an antibody is administered directly to the area of a tumor or cancer tissue, including administration directly to the tumor stroma during invasive procedures. The agent may also be placed on a solid support such as a sponge or gauze for administration and activity against CCL8.

A composition including an active component (e.g., an anti-CCL8 antibody) can be administered in conjunction with an accepted pharmaceutically acceptable carrier. Acceptable carriers include, but are not limited to, saline, buffered saline, glucose in saline. Solid supports, liposomes, nanoparticles, microparticles, nanospheres or microspheres may also be used as carriers for administration of the antibodies.

The appropriate dosage ("therapeutically effective amount") of the active component (e.g., the anti-CCL8 antibody) can depend, for example, on the particular breast cancer to be treated, the severity and course of the breast cancer, whether the agent is administered for preventive or therapeutic purposes, previous therapy, the patient's clinical history and response to the agent, the type of agent used, and the discretion of the attending physician. An active agent can be administered to a patient at one time or over a series of treatments and may be administered to the patient at any time from diagnosis onwards. An agent may be administered as the sole treatment or in conjunction with other drugs or therapies useful in treating breast cancer.

In one embodiment, a therapeutically effective amount of an agent can be in the range of about 1 ng/kg body weight/day to about 100 mg/kg body weight/day whether by one or more administrations. For example, an anti-CCL8 antibody can be administered in an amount of from about 1 ng/kg body weight/day to about 1 μg/kg body weight/day, or from about 0.5 mg/kg body weight per day to about 50 mg/kg body weight/day, in some embodiments. In other particular embodiments, the amount of an agent administered can be from about, 0.0005 mg/day to about 1000 mg/day or from about 0.1 mg/day to about 500 mg/day in some embodiments. As expected, the dosage will be dependent on the condition, size, age and condition of the patient.

An active agent may be administered, as appropriate or indicated, a single dose as a bolus or by continuous infusion, or as multiple doses by bolus or by continuous infusion. Multiple doses may be administered, for example, multiple times per day, once daily, every 2, 3, 4, 5, 6 or 7 days, weekly, every 2, 3, 4, 5 or 6 weeks or monthly. However, other dosage regimens may be useful. The progress of this therapy is easily monitored by conventional techniques.

In one embodiment, an active agent that decreases the activity of CCL8 in an area can be administered to a subject in need thereof in conjunction with one or more additional therapeutically effective agents. For instance, the active agent can be administered in conjunction with another anti-cancer agent, such as chemotherapy agent. Additional therapeutically effective agents can be administered as a component of the composition that includes the active agent that decreases the activity of CCL8 or in a separate composition, as desired.

As used herein the term "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition can be formulated to be compatible with its intended route of administration. Examples of routes of administration include parenteral, e.g., intrathecal, intra-arterial, intravenous, intradermal, subcutaneous, oral, transdermal (topical) and transmucosal administration. In certain embodiments, the pharmaceutical composition is administered directly into the tissue surrounding a tumor.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate or gelatin.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially, for example, from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form, as used herein, includes physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by, and directly dependent on, the unique characteristics of the active compound and the particular therapeutic effect to be achieved, and the limitations inherent in the art of compounding such an active compound for the treatment of individuals.

Disclosed methods and materials can be utilized in one embodiment for therapeutic interference for targeting breast cancer metastasis. Also suggested is a novel paradigm on how dissemination of the cancer cells can be attained beyond the conventional notion of EMT induction and stochastic stimulation of epithelial cell motility. Accordingly, even transient activation of CCL8 levels in peripheral tissues, such as may be caused by inflammation, may attract circulating cancer cells and trigger metastatic seeding. Presently disclosed methods and materials may be beneficial in preventing such metastatic processes.

The present invention may be better understood with reference to the Examples, set forth below.

EXAMPLE 1

Figure 3A:
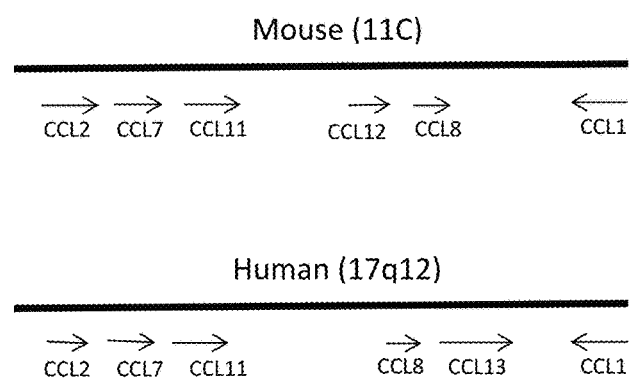
FIG. 3A schematically presents the genomic organization of the cytokine clusters that harbor CCL8 in mouse and CCL8 in humans.
Figure 3B:
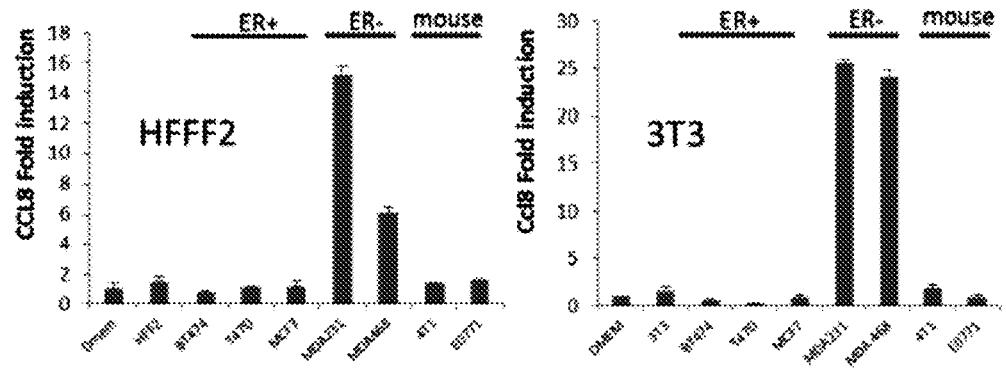
FIG. 3B illustrates CCL8 expression in mouse and human fibroblasts following exposure to breast cancer cells' conditioned media.

In order to test how breast cancer cells affect CCL8 production in the stroma, human HFFF2 and mouse 3T3 fibroblasts were exposed to conditioned media from a panel of breast cancer cells, both estrogen-dependent and estrogen-independent, and the levels of CCL8 were measured by qPCR. The results (FIG. 3B) showed that media from the triple negative breast cancers (TNBCs) MDA-MB-(MDA) 231 and MDA468 cells were stimulatory for CCL8 in both human and mouse fibroblasts while media from the estrogen-dependent MCF7, BT474, and T47D were not. This suggests that transition to estrogen-independency may be linked to the production of soluble factors that can stimulate CCL8 expression in adjacent fibroblasts.

Figure 3C:
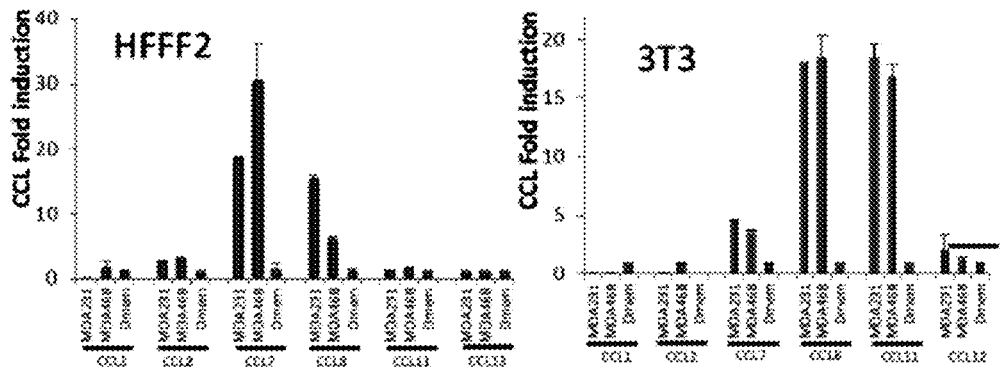
FIG. 3C presents experimental results showing that CCL8 is the only cytokine in both the human 17q12 cluster and the mouse 11C cluster that specifically responds to breast cancer cell media in both mouse and human fibroblasts.

In view of the fact that the gene encoding for CCL8 belongs to a cluster of chemoattractive cytokines (FIG. 3A) a comparison of how specific the stimulation of CCL8 is as compared to that of the other cytokines that are encoded by genes located in the same genomic cluster was carried out. As shown in FIG. 3C, besides CCL8, CCL7 in human HFFF2 and CCL11 in mouse 3T3 fibroblasts were also induced by the media from TNBCs MDA468 and MDA231 cells. However, as can be seen, CCL8 was the only cytokine that was induced in both mouse and human fibroblasts. This observation argues in favor of the important role of CCL8 in stroma-epithelium interactions, particularly those mediating the communication of TNBC cells with their microenvironment.

Figure 4A:
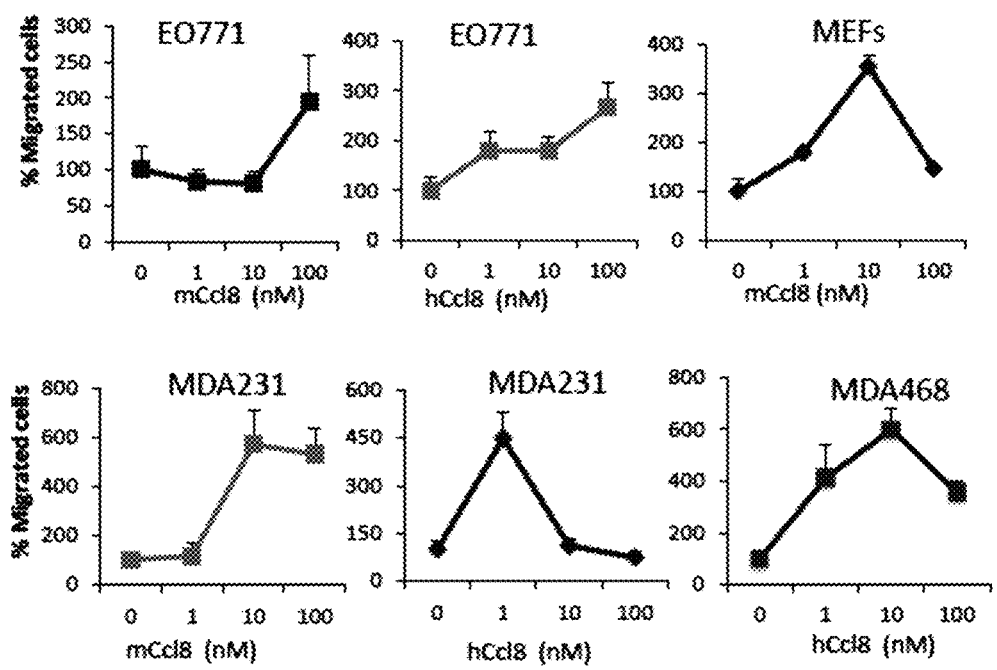
FIG. 4A graphically illustrates the chemoattraction of various breast cancer cells for fibroblasts upon increase in the amounts of CCL8 in transwells in vitro.
Figure 4B:
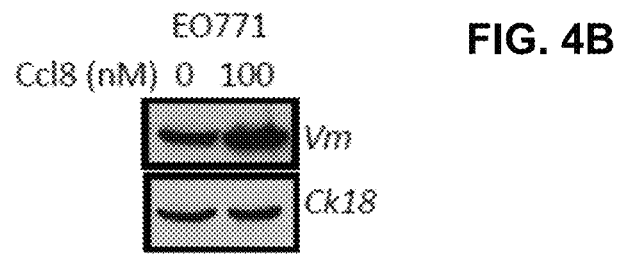
FIG. 4B illustrates the vimentin (Vm) levels in EO771 cells after treatment with CCL8 suggesting the induction of epithelial-mesenchymal transition (EMT).

The consequences of CCL8 in breast cancer cells and fibroblasts were also examined. Given the strong chemoattractive activity of CCL8 in immune cells such as the macrophages, the assessment of CCL8-induced chemoattraction for various breast cancer cells was determined. As shown in FIG. 4A, both mouse and human CCL8 attracted breast cancer cells of mouse and human origin. Besides further supporting its significant role, the observation that CCL8-induced chemoattraction is retained between the cross species barriers also suggests that human and mouse CCL8 are functionally interchangeable which is of particular value for experimental studies involving cells of different origin. Vimentin overexpression, a marker of epithelial-mesenchymal transition, in EO771 mouse breast cancer cells following CCL8 treatment (FIG. 4B), also supports the instrumental role of CCL8 in triggering a cell migration.

EXAMPLE 2

The consequences of CCL8 ablation were determined in vivo in tumor-bearing mice. First CCL8 activity was blocked by a neutralizing antibody administered daily for 1 week in mice following the inoculation of EO771 mouse breast cancer cells in the mammary fat pad of wild type mice. As shown in FIG. 5A and FIG. 5B, inhibition of CCL8 activity significantly delayed the onset of EO771 breast cancer cells in syngeneic C57BL6 mice.

The effect of genetic ablation of CCL8 in the onset of EO771 tumors in wild type (wt) and CCL8-deficient (CCL8KO) mice was then tested. The CCL8KO mice were generated by the University of California (KOMP repository). Consistently with the effects of antibody-mediated inhibition, genetic deletion of CCL8 also delayed the onset of EO771 tumors (FIG. 5C). Importantly, the source of CCL8 in these cancers was almost exclusively the stroma and not the epithelium as indicated by the virtual absence of CCL8 from the tumors of the Ccl8KO mice (FIG. 5D). Thus, host-derived CCL8 effectively modulated and indeed promoted the tumors' onset. To that end, the levels of CCL8 may reflect the degree of activation of the tumor stroma and can operate as a biomarker for disease progression. This is also supported by the positive correlation between CCL8 levels and tumor volume (FIG. 5E).

Morphological examination of the resulting tumors suggested that stromal CCL8 deficiency not only affected the kinetics but also the morphology of the tumors: EO771 breast cancers that developed in the CCL8KO mice had increased cellularity and better-defined borders (FIG. 5F) than the tumors in the wt animals. In addition, tumors in CCL8KO hosts contained poorer stroma (Van Gieson staining and smooth muscle actin (SMA) immunostaining, FIG. 5G). Thus, manipulation of CCL8 activity effectively altered tumor's morphology and especially the tumor stroma. Specifically, ablation of CCL8 inhibited the dissemination of the cancer cells suggesting the anti-metastatic activity of Ccl8 suppression.

EXAMPLE 3

Figure 6:
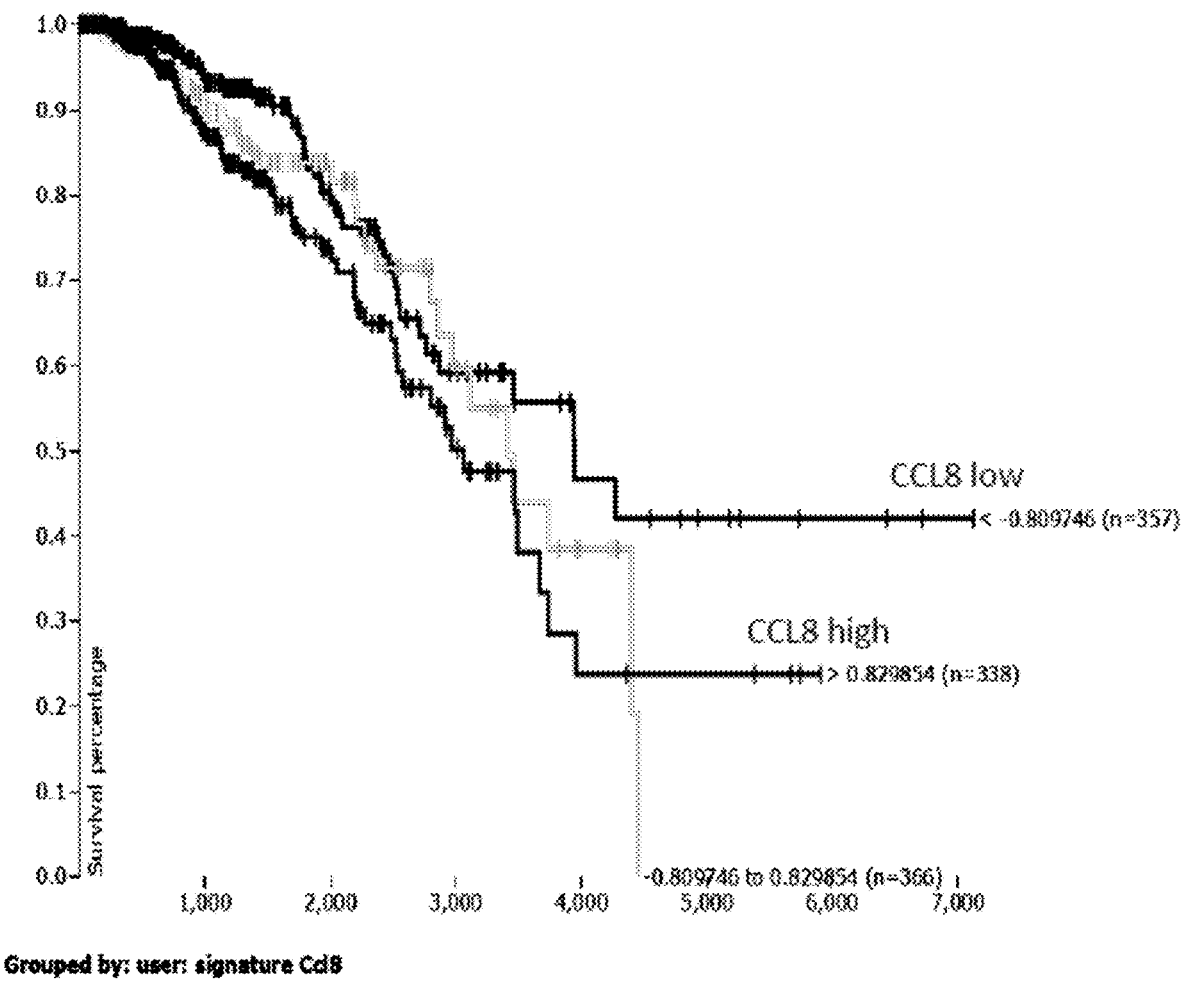
FIG. 6 illustrates an association between high CCL8 expression and negative prognosis in breast cancer patients.

Data mining for CCL8 expression in tumors of breast cancer patients was carried out. The data were obtained by the Cancer Genomics Browser (University of California at Santa Cruz, https://genome-cancer.ucsc.edu/). Analysis of these data suggests that high CCL8 expression is associated with considerably worse prognosis in breast cancer patients (FIG. 6).

EXAMPLE 4

Figure 10:
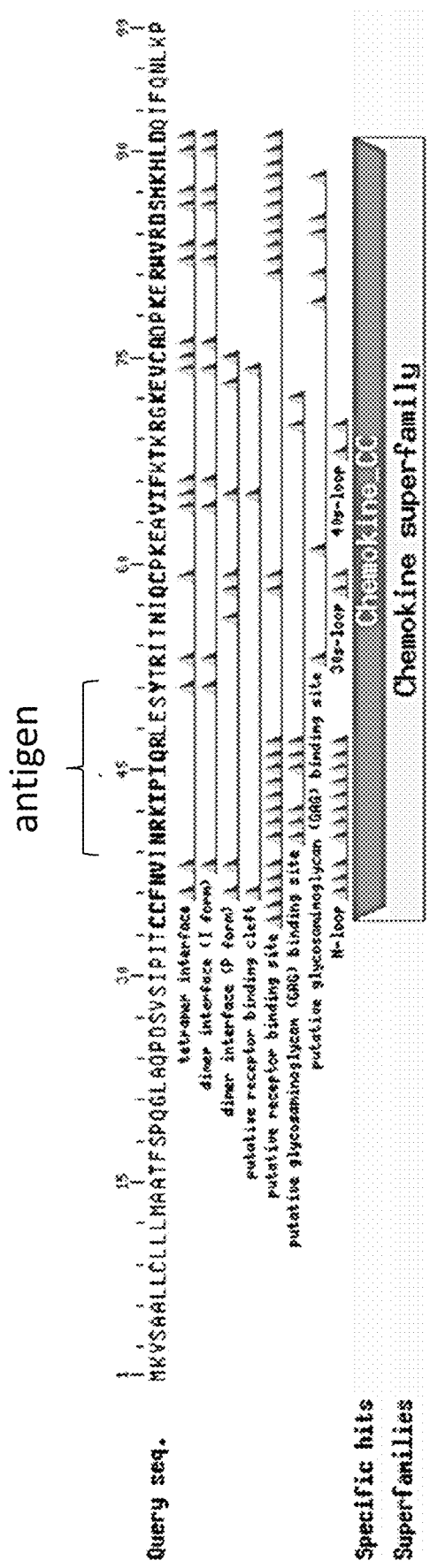
FIG. 10 provides the sequence of human CCL8 (SEQ ID NO.:2) and includes details of several elements of the sequence including the antigenic peptide described further herein.

Monoclonal antibodies were prepared against the antigen sequence CINRKIPIQRLESYT (SEQ ID NO.: 1). This antigen has similarity to human CCL7 and CCL11, but not mouse CCL8). This sequence is derived from the human CCL8 sequence (SEQ ID NO.: 2) as illustrated in FIG. 10. The immunogen was a peptide-KLG conjugate developed with a BALB/c mouse host strain. The myeloma type was SP2/0.

Elisa results of the culture supernatant are provided in Table 1, below.

TABLE 1

| Cell lines | Supernatant Dilution | | | | | | Blank | Titer | Isotype | Supernatant Concentration (µg/ml) |
|---|---|---|---|---|---|---|---|---|---|---|
| | 1:10 | 1:30 | 1:90 | 1:270 | 1:810 | 1:2430 | | | | |
| 1B5E7 | 3.135 | 3.003 | 2.596 | 2.269 | 1.693 | 1.243 | 0.054 | >1:2430 | IgG2b, κ | 16.756 |
| 1G3E5 | 2.856 | 2.769 | 2.644 | 2.394 | 2.009 | 1.351 | 0.054 | >1:2430 | IgG1, κ | 23.582 |
| 6C2B11 | 2.567 | 2.341 | 1.995 | 1.396 | 0.861 | 0.461 | 0.054 | >1:2430 | IgG2a, κ | 4.036 |
| 6C6B10 | 2.531 | 2.429 | 2.283 | 1.968 | 1.455 | 0.885 | 0.054 | >1:2430 | IgG1, κ | 12.419 |
| 6G5E6 | 2.573 | 2.379 | 2.079 | 1.600 | 0.961 | 0.563 | 0.054 | >1:2430 | IgG1, κ | 4.473 |

Figure 7:
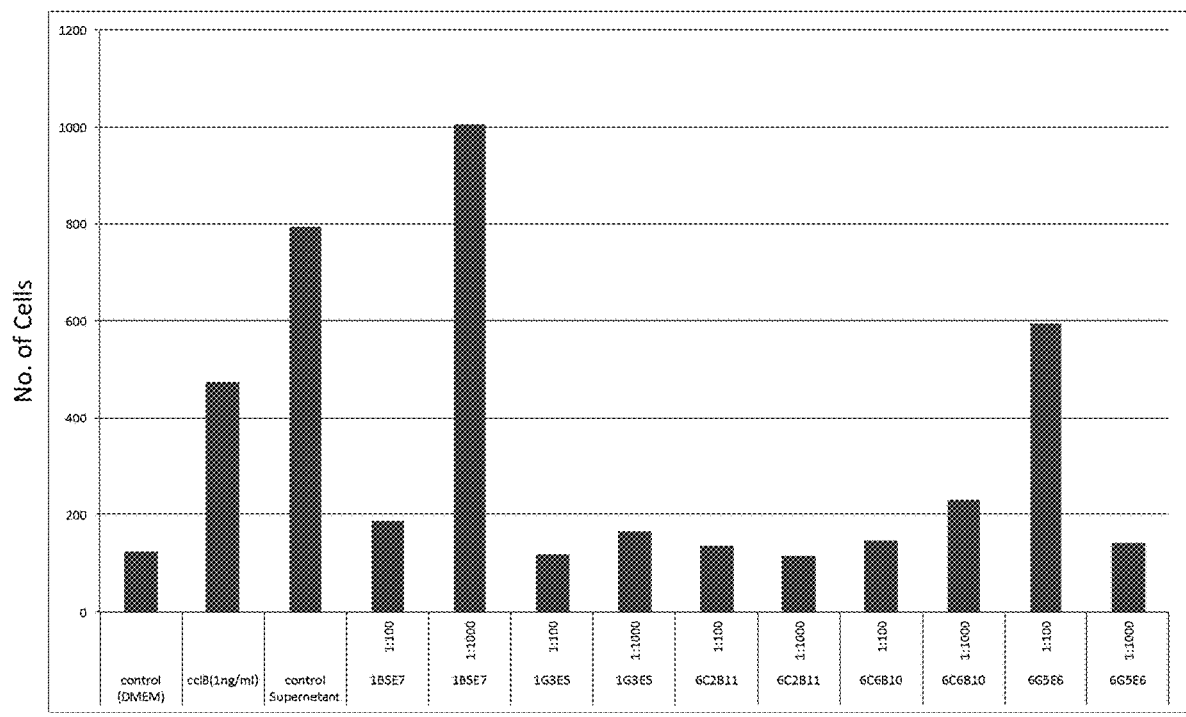
FIG. 7 graphically illustrated the migration rates of MDA-MB-231 breast cancer cells in the presence of various antibodies.

FIG. 7 graphically illustrates the migration of MDA-MB 231 breast cancer cells with human CCL8 in the transwell chambers for different monoclonal antibodies at a 1:100 and 1:1000 dilution. DMEM, CCL8 (1 ng/mL) and supernatant are included as control. As shown, the supernatant from clone 1G3E5 and 6C6B10 had the highest dose-dependent neutralizing effect.

Figure 8:
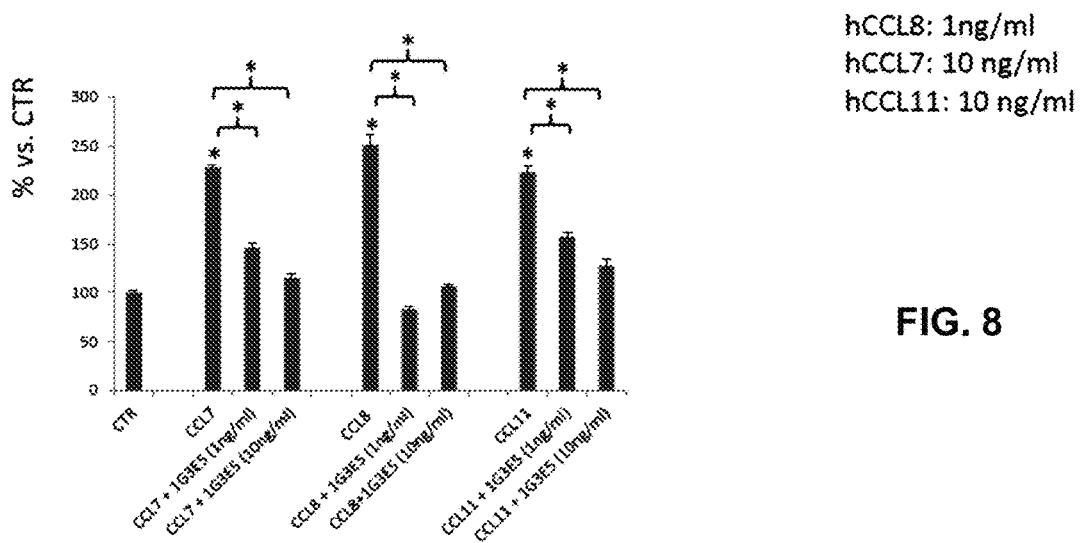
FIG. 8 illustrates migration of MDA-MB-231 breast cancer cells in the presence of various cytokines encoded by the 17q12 gene both alone and in the presence of an anti-CCL8 antibody.

The 1G3E5 clone was further examined for neutralizing effect on MDA-MB 231 breast cancer cell migration induced by human CCL7, CCL8, and CCL11. As shown in FIG. 8, this clone inhibited migration induced by all three cytokines.

Figure 9:
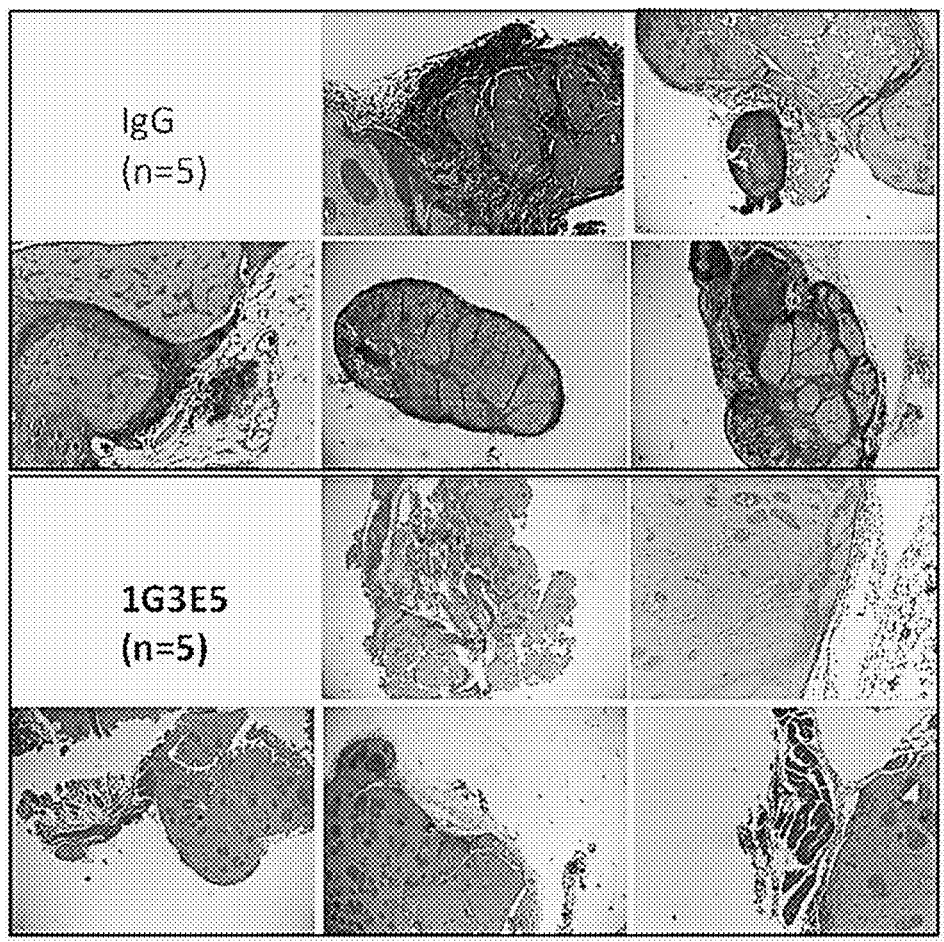
FIG. 9 presents images illustrating that the presence of anti-CCL8 antibody inhibits migration and invasion of breast cancer cells toward adjacent matrigel nodules containing CCL8-producing fibroblasts.

Morphological examination of tissue (FIG. 9) illustrated that the 1G3E5 antibody completely inhibited the migration and invasion of MDA-MB 231 bGal cancer cells toward adjacent matrigel nodules containing CCL8-producing HFF2 fibroblasts. As can be seen, the MDA-MB 231 cells (darker in the images) are completely absent from the 1G3E5-treated group (lower panels).

EXAMPLE 5

The 1G3E5 clone of Example 4 was further examined to obtain sequencing data. Hybridoma cells provided by GenScript; TRIzol® Reagent (Ambion, Cat. No.: 15596-026); PrimeScript™ 1st Strand cDNA Synthesis Kit (Takara, Cat. No.: 6110A).

Figure 11:
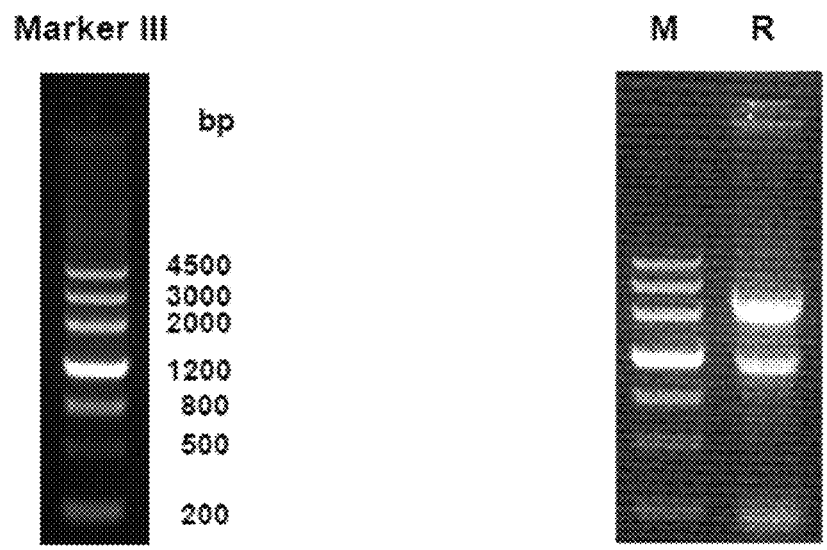
FIG. 11 illustrates results of an agarose gel electrophoresis of total RNA of a hybridoma. On the left is shown the standard and on the right are shown the results of the sample alongside the marker.

Total RNA was extracted from frozen hybridoma cells following the technical manual of TRIzol® Reagent. The total RNA was analyzed by agarose gel electrophoresis. Results are shown in FIG. 11. The isolated total RNA of the sample was run alongside a DNA marker, Marker III (TIANGEN, Cat. No.: MD103) on a 1.5% agarose/GelRed™ gel. FIG. 11, left presents the standard used for the marker and on the right is shown the results in which the lane M carried the DNA marker and lane R carried the total RNA.

Total RNA was reverse transcribed into cDNA using isotype-specific anti-sense primers or universal primers following the technical manual of PrimeScript™ 1st Strand cDNA Synthesis Kit. The antibody fragments of the variable heavy chain ($V_H$) and variable light chain ($V_L$) were amplified according to the standard operating procedure of RACE of GenScript.

Figure 12:
FIG. 12 illustrates the agarose gel electrophoresis results of PCR products of a clone as described further herein.

Amplified antibody fragments were separately cloned into a standard cloning vector using standard molecular cloning procedures. Colony PCR screening was performed to identify clones with inserts of correct sizes. Four microliters of PCR products of each sample were run alongside the DNA marker, Marker III on a 1.5% agarose/GelRed™ gel (FIG. 13). FIG. 12 includes in lane M the DNA marker, Lane 1 carried the heavy chain of the clone and Lane 2 carried the light chain of the clone. The PCR products were purified and stored at −20° C. until further use.

No less than five single colonies with inserts of correct sizes were sequenced for each antibody fragment. Individual positive clones with correct $V_H$ and $V_L$ insert sizes were sequenced. One kind of $V_H$ DNA sequence (SEQ ID NO: 3) and two kinds of $V_L$ DNA sequences (SEQ ID NO: 11, SEQ ID NO: 19) were obtained in the trial (five $V_{L1}$ and three $V_{L2}$ from eight randomly sequenced positive clones). The consensus sequences are provided herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A composition, comprising:
   an anti-CCL8 antibody or antigen binding fragment thereof comprising CDRs having SEQ ID NOs: 6, 8, 10, 14, 16, and 18; and
   a carrier.

2. The composition of claim 1, the antibody or antigen binding fragment thereof comprising SEQ ID NO: 4 and/or SEQ ID NO: 12.

3. The composition of claim 1, the carrier comprising a pharmaceutically acceptable carrier.

4. The composition of claim 1, the carrier comprising a solid support, a nanoparticle, a microparticle, a nanosphere, or a microsphere.

5. The composition of claim 1, the composition further comprising one or more additional therapeutically effective agents.

6. The composition of claim 5, the one or more additional therapeutically effective agents comprising an anti-cancer agent.

7. The composition of claim 1, wherein the composition is configured for intrathecal, intra-arterial, intravenous, intradermal, subcutaneous, oral, transdermal, or transmucosal administration.

8. The composition of claim 1, wherein the composition is in the form of a solution or a suspension.

9. The composition of claim 1, wherein the composition is configured for administration via inhalation.

10. The composition of claim 1, wherein the composition comprises the antibody or antigen binding fragment thereof in a sustained or controlled release formulation.

11. A composition comprising:
   an anti-CCL8 antibody or antigen binding fragment thereof comprising CDRs having SEQ ID NOs: 6, 8, 10, 22, 24, and 26; and
   a carrier.

12. The composition of claim 11, the antibody or antigen binding fragment thereof comprising SEQ ID NO: 4 and/or SEQ ID NO: 20.

13. The composition of claim 11, the carrier comprising a pharmaceutically acceptable carrier.

14. The composition of claim 11, the carrier comprising a solid support, a nanoparticle, a microparticle, a nanosphere, or a microsphere.

15. The composition of claim 11, the composition further comprising one or more additional therapeutically effective agents.

16. The composition of claim 15, the one or more additional therapeutically effective agents comprising an anti-cancer agent.

17. The composition of claim 11, wherein the composition is configured for intrathecal, intra-arterial, intravenous, intradermal, subcutaneous, oral, transdermal, or transmucosal administration.

18. The composition of claim 11, wherein the composition is in the form of a solution or a suspension.

19. The composition of claim 11, wherein the composition is configured for administration via inhalation.

20. The composition of claim 11, wherein the composition comprises the antibody or antigen binding fragment thereof in a sustained or controlled release formulation.

* * * * *